US00PP33774P2

(12) United States Plant Patent
Kievit et al.

(10) Patent No.: US PP33,774 P2
(45) Date of Patent: Dec. 21, 2021

(54) ***ARTEMISIA* PLANT NAMED 'BALFERNARC'**

(50) Latin Name: *Artemisia gmelinii*
Varietal Denomination: Balfernarc

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/460,254

(22) Filed: Aug. 29, 2021

(51) Int. Cl.
*A01H 5/02* (2018.01)
*A01H 6/14* (2018.01)

(52) U.S. Cl.
USPC ..... Plt./373
CPC ..... *A01H 6/14* (2018.05)

(58) Field of Classification Search
USPC ..... Plt./373
CPC ..... A01H 6/14; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Artemisia* plant named 'Balfernarc', characterized by its medium green-colored fern-like foliage and moderately vigorous, upright, compact-mounded growth habit, is disclosed.

1 Drawing Sheet

Latin name of genus and species of plant claimed: *Artemisia gmelinii.*

Variety denomination: 'Balfernarc'.

BACKGROUND OF THE INVENTION

The present invention relates to a new and distinct cultivar of *Artemisia* plant botanically known as *Artemisia gmelinii* and hereinafter referred to by the cultivar name 'Balfernarc'.

The new cultivar originated in a controlled breeding program in Hem, the Netherlands during the summer 2016. The objective of the breeding program was the development of *Artemisia* cultivars having fern-like foliage that thrive in full sun for use as an accent plant in a container or a groundcover in the landscape.

The new *Artemisia* cultivar is the result of open-pollination. The female (seed) parent of the new cultivar is the proprietary *Artemisia gmelinii* breeding selection coded A13, not patented, characterized by its medium cream-colored inflorescences, light green-colored foliage, and moderately vigorous, semi-upright growth habit. The male (pollen) parent of the new cultivar is unknown. The new cultivar was selected as a single flowering plant within the progeny of the above stated open-pollination during August 2017 in a controlled environment in Hem, the Netherlands.

Asexual reproduction of the new cultivar by terminal stem cuttings since August 2017 in Hem, the Netherlands and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balfernarc' as a new and distinct cultivar of *Artemisia* plant:

1. Medium green-colored fern-like foliage; and
2. Moderately vigorous, upright, compact-mounded growth habit.

Plants of the new cultivar differ from plants of the female parent primarily in having darker green-colored foliage and a more compact mounded growth habit.

Of the many commercially available *Artemisia* cultivars, the most similar in comparison to the new cultivar is the *Artemisia* cultivar *Artemisia* Makana Silver, 'TNARTMS', U.S. Plant Pat. No. 30,968. However, in comparison, plants of the new cultivar differ from plants of 'TNARTMS' in at least the following characteristics:

1. Plants of the new cultivar have a foliage color that is greener than plants of 'TNARTMS';
2. Plants of the new cultivar have narrower leaves than plants of 'TNARTMS'; and
3. Plants of the new cultivar have red coloration in the stems which is different from plants of 'TNARTMS'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Balfernarc'. The plants were approximately 18 weeks old. The plants were grown in three-quart containers for approximately 8 weeks in an outdoor nursery in West Chicago, Ill. Plants were given two pinches prior to transplant and one pinch one week after transplant.

DETAILED BOTANICAL DESCRIPTION

Figure 1:
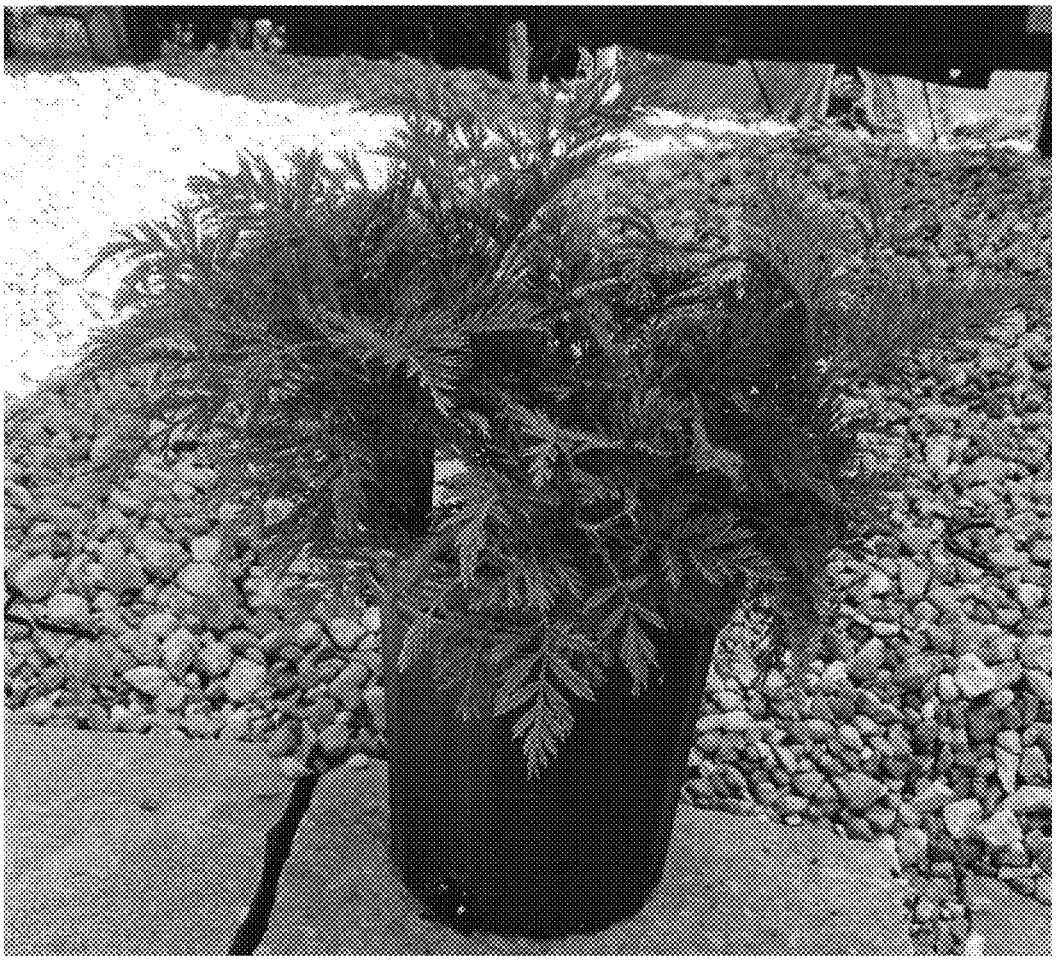
FIG. 1 illustrates a side view of the overall growth and flowering habit of 'Balfernarc'.
Figure 2:
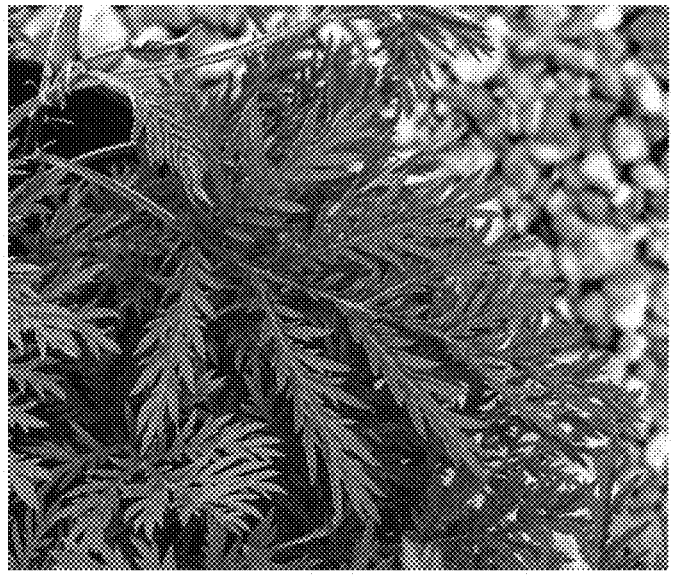
FIG. 2 illustrates a close-up view of a leaf of 'Balfernarc'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2021 under natural light conditions in Naperville, Ill.

The following descriptions and measurements describe approximately 18 weeks old plants produced from cuttings from stock plants and grown under conditions comparable to those used in commercial practice. The plants were grown in three-quart containers for approximately 8 weeks in an outdoor nursery in West Chicago, Ill. Plants were given two pinches prior to transplant and one pinch one week after transplant. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Artemisia gmelinii* 'Balfernarc'.

Parentage:

*Female parent*.—Proprietary *Artemisia gmelinii* breeding selection coded A13, not patented.

*Male parent*.—Unknown.

Propagation:

*Type cutting*.—Terminal stem, divisions of rhizome also possible.

*Time to initiate roots*.—Approximately 7 days at 70-72° F. (21-22° C.).

*Time to produce a rooted cutting*.—Approximately 35 to 42 days at 70-72° F. (21-22° C.).

*Root description*.—Fibrous, fine to medium thickness.

*Rooting habit*.—Freely branching, medium density.

Plant description:

*Commercial crop time*.—Approximately 6 to 8 weeks from a rooted cutting to finish in a one-gallon container.

*Growth habit and general appearance*.—Herbaceous perennial, moderate growth vigor, upright, compact-mounded growth habit.

*Hardiness*.—USDA Zone 4 (−30° F. to −20° F./−34.4° C. to −28.9° C.).

*Size*.—Height from soil level to top of plant plane: Approximately 19.0 cm. Width: Approximately 36.0 cm.

*Branching habit*.—Freely branching, pinching improves basal branching. Quantity: Approximately 7.

*Branches*.—Strength: Strong. Length: Approximately 12.0 cm. Diameter: Approximately 2.0 mm to 3.0 mm. Length of central internode: Approximately 1.0 cm. Texture: Moderately pubescent with a mixture of appressed hairs and clear, transparent glandular pubescence. Color of young stems: 146D. Color of mature stems: 146C with a heavy overlay of 187A, becomes woody 199A with age.

Foliage description:

*General description*.—Quantity of leaves per branch: Approximately 13. Fragrance: Strong, slightly sweet. Form: Simple, pinnatisect, bipinnately dissected. Arrangement: Spiral, dextrorse.

*Leaves*.—Aspect: Acute. Shape: Overall ovate. Margin: Serrate. Apex: Acute. Base: Overall shape truncate to rounded. Venation pattern: Pinnate. Overall length: Approximately 8.0 cm. Overall width: Approximately 6.5 cm. Length of leaflet: Approximately 3.5 cm. Width of leaflet: Approximately 1.0 cm. Texture of upper surface: Sparsely pubescent with appressed hairs, punctate glandular. Texture of lower surface: Densely appressed pubescence of 155D. Color of upper surface of young foliage: 137C with venation of 191C. Color of lower surface of young and mature foliage: Closest to 147B with venation of 191D and 146C. Color of upper surface of mature foliage: 137B with venation of 191C.

*Petiole*.—Length: Approximately 4.0 cm. Diameter: Approximately 2.0 mm. Texture: Sparsely pubescent. Color: 146D.

Flowering description:

*Flowering habit*.—'Balfernarc' requires a vernalization treatment to flower. Flowers are not observed in first year of growth. For this species, flowers are inconspicuous disc florets only and not of ornamental significance.

Seed and fruit production: Neither seed nor fruit production has been observed.

Disease and pest resistance: Resistance to pathogens and pests common to *Artemisia* has not been observed.

What is claimed is:

1. A new and distinct cultivar of *Artemisia* plant named 'Balfernarc', substantially as herein illustrated and described.

* * * * *